(12) United States Patent
Reisacher et al.

(10) Patent No.: US 9,045,644 B2
(45) Date of Patent: Jun. 2, 2015

(54) SOLID PIGMENT PREPARATIONS CONTAINING WATER-SOLUBLE SURFACE-ACTIVE POLYURETHANE-BASE ADDITIVES

(75) Inventors: Hans-Ulrich Reisacher, Maxdorf (DE); Christian Krueger, Saulheim (DE); Uwe Mauthe, Mannheim (DE); Juan Antonio Gonzalez Gomez, Ludwigshafen (DE); Raimund Schmid, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 547 days.

(21) Appl. No.: 11/815,484

(22) PCT Filed: Feb. 8, 2006

(86) PCT No.: PCT/EP2006/050761
§ 371 (c)(1),
(2), (4) Date: Aug. 3, 2007

(87) PCT Pub. No.: WO2006/084861
PCT Pub. Date: Aug. 17, 2006

(65) Prior Publication Data
US 2008/0139735 A1  Jun. 12, 2008

(30) Foreign Application Priority Data
Feb. 8, 2005 (DE) .................. 10 2005 005 846

(51) Int. Cl.
C08G 18/08 (2006.01)
C09C 3/00 (2006.01)
C09D 11/101 (2014.01)
C09D 175/14 (2006.01)
C07D 301/32 (2006.01)
C07D 303/04 (2006.01)
C08L 75/04 (2006.01)
C09B 67/00 (2006.01)
C09B 67/20 (2006.01)
C09B 67/46 (2006.01)
C09C 3/10 (2006.01)
C08L 71/00 (2006.01)

(52) U.S. Cl.
CPC .............. *C09C 3/006* (2013.01); *C09D 11/101* (2013.01); *C09D 175/14* (2013.01); *C07D 301/32* (2013.01); *C07D 303/04* (2013.01); *C08G 18/0823* (2013.01); *C08L 71/00* (2013.01); *C08L 75/04* (2013.01); *C09B 67/0022* (2013.01); *C09B 67/0063* (2013.01); *C09B 67/009* (2013.01); *C09C 3/10* (2013.01)

(58) Field of Classification Search
CPC ............................ C09D 11/101; C09D 175/14
USPC ......... 524/502, 507, 591, 839, 840; 106/400, 106/401, 499, 504, 505, 506; 428/423.1
See application file for complete search history.

(56) References Cited

U.S. PATENT DOCUMENTS

| | | | | |
|---|---|---|---|---|
| 4,234,466 | A * | 11/1980 | Takahashi et al. | 523/509 |
| 5,969,002 | A * | 10/1999 | Kijlstra et al. | 523/160 |
| 6,136,890 | A * | 10/2000 | Carlson et al. | 523/160 |
| 6,489,382 | B1 * | 12/2002 | Giesecke et al. | 524/89 |
| 6,509,409 | B1 * | 1/2003 | Thetford | 524/589 |
| 6,596,073 | B1 * | 7/2003 | Nyssen et al. | 106/499 |
| 7,172,653 | B2 * | 2/2007 | Reisacher et al. | 106/499 |
| 7,198,667 | B2 * | 4/2007 | Klopp et al. | 106/493 |
| 7,198,668 | B2 * | 4/2007 | Reisacher et al. | 106/499 |
| 7,318,864 | B2 * | 1/2008 | Reisacher et al. | 106/499 |
| 7,384,473 | B2 * | 6/2008 | Reisacher et al. | 106/499 |
| 2004/0097685 | A1 * | 5/2004 | Bruchmann et al. | 528/44 |
| 2004/0194665 | A1 | 10/2004 | Konemann et al. | |
| 2004/0260013 | A1 * | 12/2004 | Richards | 524/589 |
| 2005/0080171 | A1 * | 4/2005 | Reisacher et al. | 524/115 |
| 2005/0235876 | A1 * | 10/2005 | Reisacher et al. | 106/499 |
| 2005/0261405 | A1 * | 11/2005 | Reisacher et al. | 524/190 |
| 2006/0000392 | A1 * | 1/2006 | Reisacher et al. | 106/499 |
| 2006/0112852 | A1 * | 6/2006 | Klopp et al. | 106/31.78 |
| 2007/0186815 | A1 | 8/2007 | Weber | |

FOREIGN PATENT DOCUMENTS

| | | | |
|---|---|---|---|
| DE | 102 33 081 | 2/2004 | |
| DE | 10 2004 004 813 | 8/2004 | |
| DE | 10 2004 010 284 | 9/2005 | |
| EP | 0 438 836 | 9/1995 | |
| JP | 2002/249591 | * 9/2002 | ............... C08J 3/20 |
| WO | 99 41320 | 8/1999 | |
| WO | 99 56864 | 11/1999 | |
| WO | 02 081071 | 10/2002 | |

(Continued)

OTHER PUBLICATIONS

Borcher's Wetting and Dispersing Additives, Apr. 2005.*
English Translation of Document N.*
Partial English Translation of JP Patent Application Publication No. 2002-249591, Sep. 6, 2002, pp. 1-12.

*Primary Examiner* — Michael L Leonard
(74) *Attorney, Agent, or Firm* — Oblon, McClelland, Maier & Neustadt, L.L.P.

(57) ABSTRACT

Solid pigment preparations comprising as essential constituents (A) from 60% to 95% by weight of at least one pigment, (B) from 2.5% to 35% by weight of at least one water-soluble surface-active additive based on polyurethanes and (C) from 2.5% to 35% by weight of at least one nonionic water-soluble surface-active additive (C1) based on polyethers and/or of an anionic water-soluble additive other than additives (B) which is based on polymers of ethylenically unsaturated carboxylic acids (C2), and also production and use of the pigment preparations for coloration of macromolecular organic and inorganic materials and also of plastics.

9 Claims, No Drawings

(56) References Cited

FOREIGN PATENT DOCUMENTS

| | | |
|---|---|---|
| WO | 03 046038 | 6/2003 |
| WO | 03 064540 | 8/2003 |
| WO | 03 066743 | 8/2003 |
| WO | 2004 000903 | 12/2003 |
| WO | 2004 046251 | 6/2004 |
| WO | 2004/046251 | 6/2004 |
| WO | 2004 050770 | 6/2004 |

* cited by examiner

SOLID PIGMENT PREPARATIONS CONTAINING WATER-SOLUBLE SURFACE-ACTIVE POLYURETHANE-BASE ADDITIVES

CROSS-REFERENCE TO RELATED APPLICATIONS

This application is a 371 of PCT/EP06/050761 filed Feb. 8, 2006 and claims the benefit of DE 10 2005 005 846.9 filed Feb. 8, 2005.

The present invention relates to solid pigment preparations comprising as essential constituents
(A) from 60% to 95% by weight of at least one pigment,
(B) from 2.5% to 35% by weight of at least one water-soluble surface-active additive based on polyurethanes
and
(C) from 2.5% to 35% by weight of at least one nonionic water-soluble surface-active additive (C1) based on polyethers and/or of an anionic water-soluble additive other than additives (B) which is based on polymers of ethylenically unsaturated carboxylic acids (C2).

The present invention further relates to the production of these pigment preparations and their use for coloration of macromolecular organic and inorganic materials and also of plastics.

Liquid systems such as coatings, varnishes, emulsion paints and printing inks are customarily pigmented using pigment formulations which comprise water, organic solvent or mixtures thereof. As well as anionic, cationic, nonionic and amphoteric dispersants, these pigment formulations generally have to be additized with further assistants, such as dried-crust inhibitors, freeze resistance enhancers, thickeners and anti-skinners, for stabilization.

There is a need for novel pigment preparations which are comparable to liquid formulations with regard to color properties and dispersibility, but do not require the additions mentioned and are easier to handle. However, simply drying liquid formulations does not provide solid pigment preparations having comparable performance properties.

The coloration of plastics requires complete dispersion of the pigment in the plastic for the development of maximum color strength and color effect. For the pulverulent pigments typically used such dispersion requires appropriate know-how and a high input of shearing energy and therefore is costly. When the plastics processor does not possess this know-how and the requisite complicated and costly dispersion equipment, the colored plastics will often contain specks of incompletely dispersed pigment agglomerates, be difficult to spin and/or possess high pressure-filter values. Many plastics processors therefore employ masterbatches. A masterbatch is a typically solid, concentrated pigment formulation in a plastics matrix which is solid at room temperature and meltable and in which the pulverulent pigment is present in a state of complete dispersion and hence in a fine state of subdivision; that is, the energy needed to disperse the pulverulent pigment has already been invested to produce the masterbatch.

Pigment preparations comprising nonionic surface-active additives based on polyethers and/or water-soluble carboxylato-containing surface-active additives are known from the WO-A-03/64540, 03/66743, 04/00903, 04/50770 and 04/46251 documents. The pigment preparations described therein in some instances comprise additional additives based on acidic esters of polyethers and/or pigment derivatives as further components, but additives based on water-soluble polyurethanes are not mentioned in these documents.

The WO-A-99/56864, 03/46038 and 02/81071, EP-A-438 836 and U.S. Pat. No. 5,969,002 documents describe waterborne or solventborne pigment dispersions comprising dispersing agents based on polyurethanes. The WO-A-99/56864 and 03/46083 and also EP-A-438 836 documents are directed to preparations of a solid material which comprise the solid material (which may be a pigment) and a polyurethane-based dispersant as sole components, and WO-A-02/81071 mentions the production of solid pigment preparations by aqueous milling of pigment and dispersant and subsequent spray drying. None of these references, however, describes solid pigment preparations comprising combinations of surface-active agents.

It is an object of the present invention to provide solid pigment preparations having altogether advantageous performance properties, especially high color strength and particularly good dispersibility in a wide variety of application media, especially stir-in characteristics in liquid, preferably aqueous application media.

We have found that this object is achieved by pigment preparations comprising as essential constituents
(A) from 60% to 95% by weight of at least one pigment,
(B) from 2.5% to 35% by weight of at least one water-soluble surface-active additive based on polyurethanes
and
(C) from 2.5% to 35% by weight of at least one nonionic water-soluble surface-active additive (C1) based on polyethers and/or of an anionic water-soluble additive other than additives (B) which is based on polymers of ethylenically unsaturated carboxylic acids (C2).

The present invention further provides a process for preparing the pigment preparations, which comprises wet-comminuting the pigment (A) in an aqueous suspension which comprises some or all of the additive (B) and, if appropriate, of the additive (C) and then drying the suspension, if appropriate after the rest of the additive (B) and if appropriate (C) has been added.

The present invention further provides a process for coloration of macromolecular organic and inorganic materials, which comprises incorporating the pigment preparations in these materials by stirring or shaking.

The present invention finally provides a process for coloration of plastics, which comprises incorporating these pigment preparations in the plastics by extruding, rolling, kneading or milling.

The pigment preparations of the present invention comprise as essential constituents a pigment (A), a water-soluble surface-active additive (B) and additionally a nonionic additive (C1) and/or an anionic additive (C2).

Component (A) in the pigment preparations of the present invention comprises organic or inorganic pigments. It will be appreciated that the pigment preparations of the present invention may also comprise mixtures of various organic or various inorganic pigments or mixtures of organic and inorganic pigments.

The pigments are present in a finely divided form. Accordingly, their average particle size is typically in the range from 0.1 to 5 µm.

The organic pigments are typically organic chromatic and black pigments. Inorganic pigments can likewise be color pigments (chromatic, black and white pigments) and also luster pigments and the inorganic pigments typically used as fillers.

There now follow examples of suitable organic color pigments:

| | |
|---|---|
| monoazo pigments: | C.I. Pigment Brown 25;<br>C.I. Pigment Orange 5, 13, 36, 38, 64 and 67;<br>C.I. Pigment Red 1, 2, 3, 4, 5, 8, 9, 12, 17, 22, 23, 31, 48:1, 48:2, 48:3, 48:4, 49, 49:1, 51:1, 52:1, 52:2, 53, 53:1, 53:3, 57:1, 58:2, 58:4, 63, 112, 146, 148, 170, 175, 184, 185, 187, 191:1, 208, 210, 245, 247 and 251;<br>C.I. Pigment Yellow 1, 3, 62, 65, 73, 74, 97, 120, 151, 154, 168, 181, 183 and 191;<br>C.I. Pigment Violet 32; |
| disazo pigments: | C.I. Pigment Orange 16, 34, 44 and 72;<br>C.I. Pigment Yellow 12, 13, 14, 16, 17, 81, 83, 106, 113, 126, 127, 155, 174, 176, 180 and 188; |
| disazo condensation pigments: | C.I. Pigment Yellow 93, 95 and 128;<br>C.I. Pigment Red 144, 166, 214, 220, 221, 242 and 262;<br>C.I. Pigment Brown 23 and 41; |
| anthanthrone pigments: | C.I. Pigment Red 168; |
| anthraquinone pigments: | C.I. Pigment Yellow 147, 177 and 199;<br>C.I. Pigment Violet 31; |
| anthrapyrimidine pigments: | C.I. Pigment Yellow 108; |
| quinacridone pigments: | C.I. Pigment Orange 48 and 49;<br>C.I. Pigment Red 122, 202, 206 and 209;<br>C.I. Pigment Violet 19; |
| quinophthalone pigments: | C.I. Pigment Yellow 138; |
| diketopyrrolopyrrole pigments: | C.I. Pigment Orange 71, 73 and 81;<br>C.I. Pigment Red 254, 255, 264, 270 and 272; |
| dioxazine pigments: | C.I. Pigment Violet 23 and 37;<br>C.I. Pigment Blue 80; |
| flavanthrone pigments: | C.I. Pigment Yellow 24; |
| indanthrone pigments: | C.I. Pigment Blue 60 and 64; |
| isoindoline pigments: | C.I. Pigment Orange 61 and 69;<br>C.I. Pigment Red 260;<br>C.I. Pigment Yellow 139 and 185; |
| isoindolinone pigments: | C.I. Pigment Yellow 109, 110 and 173; |
| isoviolanthrone pigments: | C.I. Pigment Violet 31; |
| metal complex pigments: | C.I. Pigment Red 257;<br>C.I. Pigment Yellow 117, 129, 150, 153 and 177;<br>C.I. Pigment Green 8; |
| perinone pigments: | C.I. Pigment Orange 43;<br>C.I. Pigment Red 194; |
| perylene pigments: | C.I. Pigment Black 31 and 32;<br>C.I. Pigment Red 123, 149, 178, 179, 190 and 224;<br>C.I. Pigment Violet 29; |
| phthalocyanine pigments: | C.I. Pigment Blue 15, 15:1, 15:2, 15:3, 15:4, 15:6 and 16;<br>C.I. Pigment Green 7 and 36; |
| pyranthrone pigments: | C.I. Pigment Orange 51;<br>C.I. Pigment Red 216; |
| pyrazoloquinazolone pigments: | C.I. Pigment Orange 67;<br>C.I. Pigment Red 251; |
| thioindigo pigments: | C.I. Pigment Red 88 and 181;<br>C.I. Pigment Violet 38; |
| triarylcarbonium pigments: | C.I. Pigment Blue 1, 61 and 62;<br>C.I. Pigment Green 1;<br>C.I. Pigment Red 81, 81:1 and 169;<br>C.I. Pigment Violet 1, 2, 3 and 27; |
| C.I. Pigment Black 1 (aniline black); | |
| C.I. Pigment Yellow 101 (aldazine yellow); | |
| C.I. Pigment Brown 22. | |

Examples of suitable inorganic color pigments are:

| | |
|---|---|
| white pigments: | titanium dioxide (C.I. Pigment White 6), zinc white, pigment grade zinc oxide; zinc sulfide, lithopone; |
| black pigments: | iron oxide black (C.I. Pigment Black 11), iron manganese black, spinal black (C.I. Pigment Black 27); carbon black (C.I. Pigment Black 7); |
| chromatic pigments: | chromium oxide, chromium oxide hydrate green; chrome green (C.I. Pigment Green 48); cobalt green (C.I. Pigment Green 50); ultramarine green; cobalt blue (C.I. Pigment Blue 28 and 36; C.I. Pigment Blue 72); ultramarine blue; manganese blue; ultramarine violet; cobalt violet and manganese violet; red iron oxide (C.I. Pigment Red 101); cadmium sulfoselenide (C.I. Pigment Red 108); cerium sulfide (C.I. Pigment Red 265); molybdate red (C.I. Pigment Red 104); ultramarine red; brown iron oxide (C.I. Pigment Brown 6 and 7), mixed brown, spinel phases and corundum phases (C.I. Pigment Brown 29, 31, 33, 34, 35, 37, 39 and 40), chromium titanium yellow (C.I. Pigment Brown 24), chrome orange; cerium sulfide (C.I. Pigment Orange 75); yellow iron oxide (C.I. Pigment Yellow 42); nickel titanium yellow (C.I. Pigment Yellow 53; C.I. Pigment Yellow 157, 158, 159, 160, 161, 162, 163, 164 and 189); chromium titanium yellow; spinel phases (C.I. Pigment Yellow 119); cadmium sulfide and cadmium zinc sulfide (C.I. Pigment Yellow 37 and 35); chrome yellow (C.I. Pigment Yellow 34); bismuth vanadate (C.I. Pigment Yellow 184). |

Examples of inorganic pigments typically used as fillers are transparent silicon dioxide, ground quartz, aluminum oxide, aluminum hydroxide, natural micas, natural and precipitated chalk and barium sulfate.

Luster pigments are platelet-shaped pigments having a monophasic or polyphasic construction whose color play is marked by the interplay of interference, reflection and absorption phenomena. Examples are aluminum platelets and aluminum, iron oxide and mica platelets bearing one or more coats, especially of metal oxides.

Component (B) of the pigment preparations according to the present invention comprises water-soluble surface-active additives based on polyurethanes.

For the purposes of the present invention, the term "polyurethanes" shall comprehend not just the pure reaction products of polyfunctional isocyanates (Ba) with isocyanate reactive hydroxyl-comprising organic compounds (Bb), but also these reaction products after additional functionalization through the addition of further isocyanate reactive compounds, examples being carboxylic acids bearing primary or secondary amino groups.

These additives are notable for their low ionic conductivity and their neutral pH compared with other surface-active additives.

Useful polyfunctional isocyanates (Ba) for preparing the additives (B) are in particular diisocyanates, but compounds having three or four isocyanate groups can be used as well. Both aromatic and aliphatic isocyanates may be used.

Examples of preferred di- and triisocyanates are: 2,4-tolylene diisocyanate (2,4-TDI), 4,4'-diphenylmethane diisocyanate (4,4'-MDI), para-xylylene diisocyanate, 1,4-diisocyanatobenzene, tetramethylxylylene diisocyanate (TMXDI), 2,4'-diphenylmethane diisocyanate (2,4'-MDI) and triisocyanatotoluene and also isophorone diisocyanate (IPDI), 2-butyl-2-ethylpentamethylene diisocyanate, tetramethylene diisocyanate, hexamethylene diisocyanate, dodecamethylene diisocyanate, 2,2-bis(4-isocyanatocyclohexyl)propane, trimethylhexane diisocyanate, 2-isocyanatopropylcyclohexyl isocyanate, 2,4,4-trimethylhexamethylene diisocyanate, 2,2, 4-trimethylhexamethylene diisocyanate, 2,4'-methylenebis (cyclohexyl) diisocyanate, cis-cyclohexane 1,4-diisocyanate, trans-cyclohexane 1,4-diisocyanate and 4-methylcyclohexane 1,3-diisocyanate (H-TDI).

It will be appreciated that mixtures of isocyanates (Ba) may also be used. There may be mentioned by way of example: mixtures of structural isomers of 2,4-tolylene diisocyanate and triisocyanatotoluene, examples being mixtures of 80 mol % of 2,4-tolylene diisocyanate and 20 mol % of 2,6-tolylene diisocyanate; mixtures of cis- and trans-cyclohexane 1,4-diisocyanate; mixtures of 2,4- or 2,6-tolylene diisocyanate with aliphatic diisocyanates, such as hexamethylene diisocyanate and isophorone diisocyanate.

Useful isocyanate reactive compounds (Bb) preferably include compounds having at least two isocyanate reactive hydroxyl groups per molecule. Compounds useful as (Bb), however, further include compounds having only one isocyanate reactive hydroxyl group per molecule. These monofunctionalized compounds can partly or else wholly replace the compounds which comprise at least two isocyanate reactive hydroxyl groups per molecule, in the reaction with the polyisocyanate (Ba).

Examples of particularly preferred isocyanate reactive compounds (Bb) having at least two isocyanate reactive hydroxyl groups per molecule will now be recited.

They are polyetherdiols, polyesterdiols, lactone-based polyesterdiols, diols and triols of up to 12 carbon atoms, dihydroxy carboxylic acids, dihydroxy sulfonic acids, dihydroxy phosphonic acids, polycarbonatediols, polyhydroxyolefins and polysiloxanes having on average at least two hydroxyl groups per molecule.

Useful polyetherdiols (Bb) include for example homo- and copolymers of $C_2$-$C_4$-alkylene oxides, such as ethylene oxide, propylene oxide and butylene oxide, tetrahydrofuran, styrene oxide and/or epichlorohydrin, which are obtainable in the presence of a suitable catalyst, an example being boron trifluoride. Further useful polyetherdiols are obtainable by (co)polymerization of these compounds in the presence of a starter having at least two acidic hydrogen atoms, examples of a starter being water, ethylene glycol, thioglycol, mercaptoethanol, 1,3-propanediol, 1,4-butanediol, 1,6-hexanediol, 1,12-dodecanediol, ethylenediamine, aniline or 1,2-di-(4-hydroxyphenyl)propane.

Examples of particularly suitable polyetherdiols (Bb) are polyethylene glycol, polypropylene glycol, polybutylene glycol and polytetrahydrofuran and also copolymers thereof.

The molecular weight $M_n$ of the polyetherdiols is preferably in the range from 250 to 5000 and more preferably in the range from 500 to 2500.

Useful isocyanate reactive compounds (Bb) further include polyesterdiols (hydroxy polyesters), which are common knowledge.

Preferred polyesterdiols (Bb) are the reaction products of diols with dicarboxylic acids or their reactive derivatives, examples being anhydrides or dimethyl esters.

Useful dicarboxylic acids include saturated and unsaturated aliphatic and also aromatic dicarboxylic acids which may bear additional substituents, such as halogen. Preferred aliphatic dicarboxylic acids are saturated unbranched α,ω-dicarboxylic acids comprising from 3 to 22 and in particular from 4 to 12 carbon atoms.

Examples of particularly suitable dicarboxylic acids are: succinic acid, glutaric acid, adipic acid, suberic acid, azelaic acid, sebacic acid, 1,12-dodecanedicarboxylic acid, maleic acid, maleic anhydride, fumaric acid, itaconic acid, phthalic acid, isophthalic acid, phthalic anhydride, tetrahydrophthalic anhydride, hexahydrophthalic anhydride, tetrachlorophthalic anhydride, endomethylenetetrahydrophthalic anhydride, terephthalic acid, dimethyl terephthalate and dimethyl isophthalate.

Useful diols include in particular saturated and unsaturated aliphatic and cycloaliphatic diols. The aliphatic α,ω-diols which are particularly preferred are unbranched and have from 2 to 12, in particular from 2 to 8 and especially from 2 to 4 carbon atoms. Preferred cycloaliphatic diols are derived from cyclohexane.

Examples of particularly suitable diols are: ethylene glycol, propylene glycol, 1,3-propanediol, 1,4-butanediol, 2-methylpropane-1,3-diol, 1,5-pentanediol, neopentyl glycol, 1,6-hexanediol, 1,8-octanediol, 1,10-decanediol, 1,12-dodecanediol, cis-but-2-ene-1,4-diol, trans-but-2-ene-1,4-diol, 2-butyne-1,4-diol, cis-1,4-di(hydroxymethyl)-cyclohexane and trans-1,4-di(hydroxymethyl)cyclohexane.

The molecular weight $M_n$ of the polyesterdiols is preferably in the range from 300 to 5000.

Lactone-based polyesterdiols useful as an isocyanate reactive compound (Bb) are based in particular on aliphatic saturated unbranched ω-hydroxy carboxylic acids having from 4 to 22 and preferably from 4 to 8 carbon atoms. It is also possible to use branched ω-hydroxy carboxylic acids wherein one or more $—CH_2—$ groups in the alkylene chain are replaced by $—CH(C_1$-$C_4$-alkyl)-$.

Examples of preferred ω-hydroxy carboxylic acids are γ-hydroxybutyric acid and δ-hydroxyvaleric acid.

It will be appreciated that the abovementioned diols may likewise be used as isocyanate reactive compounds (Bb), in which case the same preferences as above apply.

Triols, in particular triols having from 3 to 12 carbon atoms and especially triols having from 3 to 8 carbon atoms are likewise useful as isocyanate reactive compounds (Bb). Trimethylolpropane is an example of a particularly suitable triol.

Dihydroxy carboxylic acids useful as isocyanate reactive compounds (Bb) are in particular aliphatic saturated dihydroxy carboxylic acids which preferably comprise 4 to 14 carbon atoms. Dihydroxy carboxylic acids of the formula

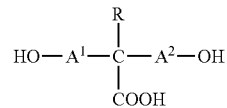

where $A^1$ and $A^2$ represent identical or different $C_1$-$C_4$-alkylene radicals and R represents hydrogen or $C_1$-$C_4$-alkyl, are very particularly suitable.

Dimethylolpropionic acid (DMPA) is a particularly preferred example of these dihydroxy carboxylic acids.

Useful isocyanate-reactive compounds (Bb) further include the corresponding dihydroxy sulfonic acids and dihydroxy phosphonic acids, such as 2,3-dihydroxypropanephosphonic acid.

Dihydroxy carboxylic acid as used herein shall also comprise compounds comprising more than one carboxyl function (or as the case may be anhydride or ester function). Such compounds are obtainable by reaction of dihydroxy compounds with tetracarboxylic dianhydrides, such as pyromellitic dianhydride or cyclopentanetetra-carboxylic dianhydride, in a molar ratio from 2:1 to 1.05:1 in a polyaddition reaction, and preferably have an average molecular weight $M_n$ in the range from 500 to 10 000.

Examples of useful polycarbonatediols (Bb) are the reaction products of phosgene with an excess of diols, in particular unbranched saturated aliphatic α,ω-diols having from 2 to 12, in particular from 2 to 8 and especially from 2 to 4 carbon atoms.

Polyhydroxyolefins useful as an isocyanate-reactive compound (Bb) are in particular α,ω-dihydroxyolefins, and α,ω-dihydroxybutadienes are preferred.

The polysiloxanes useful as an isocyanate-reactive compound (Bb) comprise on average at least two hydroxyl groups per molecule. Particularly suitable polysiloxanes comprise on average from 5 to 200 silicon atoms (number average) and are in particular substituted by $C_1$-$C_{12}$-alkyl groups, in particular methyl groups.

Examples of isocyanate-reactive compounds (Bb) comprising just one isocyanate reactive hydroxyl group are in particular aliphatic, cycloaliphatic and araliphatic or aromatic monohydroxy carboxylic acids and monohydroxy sulfonic acids.

The polyurethane-based additives comprised in the pigment preparations of the present invention as component (B) are prepared by reaction of the compounds (Ba) and (Bb) in a molar ratio of (Ba) to (Bb) which is generally in the range from 2:1 to 1:1 and preferably in the range from 1.2:1 to 1:1.2.

It is possible in this connection, as well as the aforementioned isocyanate reactive compounds (Bb), to add further compounds having isocyanate reactive groups, for example dithiols, thio alcohols, such as thioethanol, amino alcohols, such as ethanolamine and N-methylethanolamine, or diamines, such as ethylenediamine, to thereby prepare polyurethanes which, as well as urethane groups, additionally bear isocyanurate groups, allophanate groups, urea groups, biuret groups, uretidione groups or carbodiimide groups. Further examples of such isocyanate reactive compounds are aliphatic, cycloaliphatic, araliphatic or aromatic carboxylic acids and sulfonic acids which bear at least two primary and/or secondary amino groups.

It will be appreciated that it is also possible to add corresponding compounds having just one isocyanate reactive group, examples being monoalcohols, primary and secondary monoamines, monoamino carboxylic and sulfonic acids and mercaptans. Customary use levels range up to 10 mol %, based on (Ba).

Preferably, some or all of the carboxyl groups of the reaction products (B) are in salt form in order that solubility in water may be ensured. Useful salts include for example alkali metal salts, such as sodium and potassium salts, and ammonium salts. Typically, the additives (B) have average molecular weights $M_w$ in the range from 500 to 250 000.

Specific surface-active properties can be achieved for the additives (B) via the ratio of polar to apolar groups.

Such anionic surface-active additives (B) are known and commercially available, for example under the name Borchi® GEN SN95 (Borchers).

The pigment preparations of the present invention further comprise a further surface-active additive (C). The further surface-active additive (C) may be not only a nonionic water-soluble surface-active additive (C1) based on polyethers but also an anionic water-soluble surface-active additive (C2) based on polymers of ethylenically unsaturated carboxylic acids. It will be appreciated that mixtures of various additives (C1) or (C2) and mixtures of additives (C1) and (C2) may also be comprised.

The combination of additive (B) and additive (C) provides pigment preparations which are particularly easy to handle and meter.

As well as unmixed polyalkylene oxides, preferably $C_2$-$C_4$-alkylene oxides and phenyl-substituted $C_2$-$C_4$-alkylene oxides, especially polyethylene oxides, polypropylene oxides and poly(phenylethylene oxides), it is in particular block copolymers, especially polymers having polypropylene oxide and polyethylene oxide blocks or poly(phenylethylene oxide) and polyethylene oxide blocks, and also random copolymers of these alkylene oxides which are suitable for use as nonionic additives (C1).

These polyalkylene oxides are preparable by polyaddition of alkylene oxides onto starter molecules, as onto saturated or unsaturated aliphatic and aromatic alcohols, phenol or naphthol, which can be substituted in each case by alkyl, in particular $C_1$-$C_{12}$-alkyl, preferably $C_4$-$C_{12}$ or $C_1$-$C_4$ alkyl, saturated or unsaturated aliphatic and aromatic amines, saturated or unsaturated aliphatic carboxylic acids and carboxamides. It is customary to use from 1 to 300 mol and preferably from 3 to 150 mol of alkylene oxide per mole of starter molecule.

Suitable aliphatic alcohols comprise in general from 6 to 26 carbon atoms and preferably from 8 to 18 carbon atoms and can have an unbranched, branched or cyclic structure. Examples are octanol, nonanol, decanol, isodecanol, undecanol, dodecanol, 2-butyloctanol, tridecanol, isotridecanol, tetradecanol, pentadecanol, hexadecanol (cetyl alcohol), 2-hexyldecanol, heptadecanol, octadecanol (stearyl alcohol), 2-heptylundecanol, 2-octyldecanol, 2-nonyltridecanol, 2-decyltetradecanol, oleyl alcohol and 9-octadecanol and also mixtures of these alcohols, such as $C_8/C_{10}$, $C_{13}/C_{15}$ and $C_{16}/C_{18}$ alcohols, and cyclopentanol and cyclohexanol. Of particular interest are the saturated or unsaturated fatty alcohols obtained from natural raw materials by fat lypolysis and reduction and the synthetic fatty alcohols from the oxo process. The alkylene oxide adducts with these alcohols typically have average molecular weights $M_n$ from 200 to 5000.

Examples of the abovementioned aromatic alcohols include not only unsubstituted phenol and α- and β-naphthol but also hexylphenol, heptylphenol, octylphenol, nonylphenol, isononylphenol, undecylphenol, dodecylphenol, di- and tributylphenol and dinonylphenol.

Suitable aliphatic amines correspond to the abovementioned aliphatic alcohols. Again of particular importance here are the saturated and unsaturated fatty amines which preferably have from 14 to 20 carbon atoms. Examples of suitable aromatic amines are aniline and its derivatives.

Useful aliphatic carboxylic acids include especially saturated and unsaturated fatty acids which preferably comprise from 14 to 20 carbon atoms and fully hydrogenated, partially hydrogenated and unhydrogenated resin acids and also polyfunctional carboxylic acids, for example dicarboxylic acids, such as maleic acid.

Suitable carboxamides are derived from these carboxylic acids.

As well as alkylene oxide adducts with monofunctional amines and alcohols it is alkylene oxide adducts with at least bifunctional amines and alcohols which are of very particular interest.

The at least bifunctional amines preferably have from 2 to 5 amine groups and conform in particular to the formula $H_2N$—$(R^1$—$NR^2)_n$—$H(R^1$: $C_2$-$C_6$-alkylene; $R^2$: hydrogen or $C_1$-$C_6$-alkyl; n: 1-5). Specific examples are: ethylenediamine, diethylenetriamine, triethylenetetramine, tetraethylenepentamine, 1,3-propylenediamine, dipropylenetriamine, 3-amino-1-ethyleneaminopropane, hexamethylenediamine, dihexamethylenetriamine, 1,6-bis(3-aminopropylamino)hexane and N-methyldipropylenetriamine, of which hexamethylenediamine and diethylenetriamine are more preferable and ethylenediamine is most preferable.

These amines are preferably reacted first with propylene oxide and then with ethylene oxide. The ethylene oxide content of the block copolymers is typically about 10% to 90% by weight.

The average molecular weights $M_n$ of the block copolymers based on polyamines are generally in the range from 1000 to 40 000 and preferably in the range from 1500 to 30 000.

The at least bifunctional alcohols preferably have from two to five hydroxyl groups. Examples are $C_2$-$C_6$-alkylene glycols and the corresponding di- and polyalkylene glycols, such as ethylene glycol, 1,2-propylene glycol, 1,3-propylene glycol, 1,2-butylene glycol, 1,4-butylene glycol, 1,6-hexylene glycol, dipropylene glycol and polyethylene glycol, glycerol and pentaerythritol, of which ethylene glycol and polyethylene glycol are more preferable and propylene glycol and dipropylene glycol are most preferable.

Particularly preferred alkylene oxide adducts with at least bifunctional alcohols have a central polypropylene oxide block, ie are based on a propylene glycol or polypropylene glycol which is initially reacted with further propylene oxide and then with ethylene oxide. The ethylene oxide content of the block copolymers is typically in the range from 10% to 90% by weight.

The average molecular weights $M_n$ of the block copolymers based on polyhydric alcohols are generally in the range from 1000 to 20 000 and preferably in the range from 1000 to 15 000. Such alkylene oxide block copolymers are known and commercially available for example under the names of Tetronic® and Pluronic® (BASF).

Useful anionic water-soluble surface-active additives based on polymers of ethylenically unsaturated carboxylic acids (C2) are in particular additives from the group of homo- and copolymers of ethylenically unsaturated monocarboxylic acids, and/or homo- and copolymers of ethylenically unsaturated dicarboxylic acids, which may each further comprise interpolymerized vinyl monomers comprising no acid function, alkoxylation products of these homo- and copolymers and salts of these homo- and copolymers and of their alkoxylation products.

As examples of carboxyl-containing monomers and of vinyl monomers there may be mentioned:
  acrylic acid, methacrylic acid and crotonic acid;
  maleic acid, maleic anhydride, maleic monoesters, maleic monoamides, reaction products of maleic acid with diamines, which may be oxidized to form derivatives comprising amine oxide groups, and fumaric acid, of which maleic acid, maleic anhydride and maleic monoamides are preferred;
  vinylaromatics, such as styrene, methylstyrene and vinyltoluene; ethylene, propylene, isobutene, diisobutene and butadiene; vinyl ethers, such as polyethylene glycol monovinyl ether; vinyl esters of linear or branched monocarboxylic acids, such as vinyl acetate and vinyl propionate; alkyl esters and aryl esters of ethylenically unsaturated monocarboxylic acids, in particular acrylic and methacrylic esters, such as methyl acrylate, ethyl acrylate, propyl acrylate, isopropyl acrylate, butyl acrylate, pentyl acrylate, hexyl acrylate, 2-ethylhexyl acrylate, nonyl acrylate, lauryl acrylate, hydroxyethyl acrylate, methyl methacrylate, ethyl methacrylate, propyl methacrylate, isopropyl methacrylate, butyl methacrylate, pentyl methacrylate, hexyl methacrylate, 2-ethylhexyl methacrylate, nonyl methacrylate, lauryl methacrylate and hydroxyethyl methacrylate and also phenyl acrylate, phenyl (meth)acrylate, naphthyl acrylate, naphthyl (meth)acrylate, benzyl acrylate and benzyl (meth)acrylate; dialkyl esters of ethylenically unsaturated dicarboxylic acids, such as dimethyl maleate, diethyl maleate, dipropyl maleate, diisopropyl maleate, dibutyl maleate, dipentyl maleate, dihexyl maleate, di-2-ethylhexyl maleate, dinonyl maleate, dilauryl maleate, di-2-hydroxyethyl maleate, dimethyl fumarate, diethyl fumarate, dipropyl fumarate, diisopropyl fumarate, dibutyl fumarate, dipentyl fumarate, dihexyl fumarate, di-2-ethylhexyl fumarate, dinonyl fumarate, dilauryl fumarate, di-2-hydroxyethyl fumarate; vinylpyrrolidone; acrylonitrile and methacrylonitrile; of which styrene, isobutene, diisobutene, acrylic esters and polyethylene glycol monovinyl ether are preferred.

Polyacrylic acids in particular are to be mentioned as examples of preferred homopolymers of these monomers.

The copolymers of the monomers mentioned may be constructed of two or more and in particular three different monomers. The copolymers may be random, alternating, block or graft. Preferred copolymers are styrene-acrylic acid, acrylic acid-maleic acid, acrylic acid-methacrylic acid, butadiene-acrylic acid, isobutene-maleic acid, diisobutene-maleic acid and styrene-maleic acid copolymers, which may each comprise acrylic esters and/or maleic esters as additional monomeric constituents.

Preferably, the carboxyl groups of nonalkoxylated homo- and copolymers are wholly or partly present in salt form in order that solubility in water may be ensured. The alkali metal salts, such as sodium and potassium salts, and the ammonium salts are suitable for example.

The nonalkoxylated polymeric additives (B) will typically have average molecular weights $M_w$ in the range from 900 to 250 000. The molecular weight ranges particularly suitable for the individual polymers depend on their composition, of course. The molecular weight data which follow for various polymers are given by way of example: polyacrylic acids: $M_w$ from 900 to 250 000; styrene-acrylic acid copolymers: $M_w$ from 1000 to 50 000; acrylic acid-methacrylic acid copolymers: $M_w$ from 1000 to 250 000; acrylic acid-maleic acid copolymers: $M_w$ from 2000 to 70 000.

As well as these homo- and copolymers themselves, their alkoxylation products are also of particular interest for use as additives (C2).

Alkoxylation products in this context refers according to the present invention in particular to the polymers after their partial to (if possible) complete esterification with polyether alcohols. The degree of esterification of these polymers is generally in the range from 30 to 80 mol %.

Useful polyether alcohols for the esterification are in particular the polyether alcohols themselves, preferably polyethylene glycols and polypropylene glycols, and also their unilaterally end-capped derivatives, in particular the corresponding monoethers, such as monoaryl ethers, for example monophenyl ethers, and in particular mono-$C_1$-$C_{26}$-alkyl ethers, for example ethylene and propylene glycols etherified with fatty alcohols, and the polyetheramines which are preparable for example by conversion of a terminal OH group of the corresponding polyether alcohols or by polyaddition of alkylene oxides onto preferably primary aliphatic amines. Preference here is given to polyethylene glycols, polyethylene glycol monoethers and polyetheramines. The average molecular weights $M_n$ of the polyether alcohols used and of their derivatives is typically in the range from 200 to 10 000.

Specific surface-active properties can be achieved for the additives (C2) by varying the ratio of polar to apolar groups.

Such anionic surface-active additives (C2) are likewise known and commercially available, for example under the names Sokalan® (BASF), Joncryl® (Johnson Polymer), Alcosperse® (Alco), Geropone® (Rhodia), Good-Rite®

(Goodrich), Neoresin® (Avecia), Orotan® and Morez® (Rohm & Haas), Disperbyk® (Byk) and also Tegospers® (Goldschmidt).

The pigment preparations of the present invention comprise from 60% to 95% by weight of component (A), from 2.5% to 40% by weight of component (B) and from 2.5% to 20% by weight of component (C).

Preferably, the composition of the pigment preparations is from 60% to 85% by weight of pigment (A), from 5% to 20% by weight of additive (B) and from 5% to 20% by weight of additive (C), the sum total of components (A), (B) and (C) being 100% by weight.

The pigment preparations of the present invention are advantageously obtainable by the production process of the present invention, by wet-comminuting the pigment (A) in an aqueous suspension which comprises some or all of the additive (B) and, if appropriate, of the additive (C) and then drying the suspension, if appropriate after the rest of the additive (B) and if appropriate (C) has been added.

The pigment (A) can be employed in the process of the present invention as a dry powder or in the form of a press cake.

The employed pigment (A) is preferably a finished product, i.e., the primary particle size of the pigment has already been set to the desired value for the planned application. This pigment finish is especially advisable in the case of organic pigments, since the as-synthesized crude pigment is generally not directly suitable for the planned application. In the case of inorganic pigments, examples being oxide and bismuth vanadate pigments, the primary particle size can also be set in the course of the synthesis of the pigment, so that the pigment suspensions obtained can be employed directly in the process of the present invention.

Since the finished pigment (A) typically reagglomerates again in the course of drying or on the filter assembly, it is subjected to wet comminution, for example grinding in a stirred media mill, in aqueous suspension.

The wet comminution should be carried out with some or all of the additive (B and if appropriate C) comprising the ready-produced pigment preparation; it is preferable to add the entire amount of additive (B and if appropriate C) prior to the wet comminution.

The particle size of the pigment preparations of the present invention can be controlled to a specifically targeted value, depending on the method which is chosen for drying-spray granulation and fluidized bed drying, spray drying, drying in a paddle dryer, evaporation and subsequent comminution.

Spray and fluidized bed granulation may produce coarsely divided granules having average particle sizes from 50 to 5000 µm and especially from 100 to 1000 µm. Spray drying typically produces granules having average particle sizes <20 µm. Finely divided preparations are obtainable by drying in a paddle dryer and by evaporation with subsequent grinding. Preferably, however, the pigment preparations of the present invention are in granule form.

Spray granulation is preferably carried out in a spray tower using a one-material nozzle. Here, the suspension is sprayed in the form of relatively large drops, and the water evaporates. The additive melts at the drying temperatures and so leads to the formation of a substantially spherical granule having a particularly smooth surface (BET values generally <15 m$^2$/g, and especially <10 m$^2$/g).

The gas inlet temperature in the spray tower is generally in the range from 180 to 300° C. and preferably in the range from 150 to 300° C. The gas outlet temperature is generally in the range from 70 to 150° C. and preferably in the range from 70 to 130° C.

The residual moisture content of the granular pigment obtained is preferably <2% by weight.

The pigment preparations of the present invention are notable in application media comprising a liquid phase for their excellent color properties which are comparable to those of liquid pigment formulations, especially with regard to color strength, brilliance, hue and hiding power, and in particular for their stir-in characteristics, ie they can be dispersed in application media with a minimal input of energy, simply by stirring or shaking. This applies in particular to the coarsely divided pigment granules, which constitute the preferred embodiment of the pigment preparations of the present invention.

Compared with liquid pigment formulations, the pigment preparations of the present invention additionally have the following advantages: They have a higher pigment content. Whereas liquid formulations tend to change viscosity during storage and have to be admixed with preservatives and agents for enhancing the resistance to freezing and/or drying out (crusting), the pigment preparations of the present invention exhibit very good stability in storage. They are both economically and ecologically advantageous with regard to packaging, storage and transportation. Since they are solvent free, they are more flexible in use.

The pigment preparations of the present invention which are in granule form are notable for excellent attrition resistance, a minimal tendency to compact or clump, uniform particle size distribution, good pourability, flowability and meterability and also dustlessness in handling and application.

The pigment preparations of the present invention are very useful for pigmenting macromolecular organic and inorganic materials of any kind. Liquid application media in this context can also be purely aqueous; comprise mixtures of water and organic solvents, for example alcohols; or be based exclusively on organic solvents, such as alcohols, glycol ethers, ketones, eg methyl ethyl ketone, amides, eg N-methylpyrrolidone and dimethylformamide, esters, eg ethyl acetate, butyl acetate and methoxypropyl acetate, or aromatic or aliphatic hydrocarbons, eg xylene, mineral oil and mineral spirits.

If desired, the preparations can initially be stirred into a solvent which is compatible with the particular application medium, and this stirring into the solvent is again possible with minimal input of energy, and then be introduced into this application medium. For instance, slurries of pigment preparations in glycols or other solvents customary in the paint and coatings industry, such as methoxypropyl acetate, can be used to render the pigment preparations adapted to aqueous systems compatible with hydrocarbonaceous systems or systems based on nitrocellulose.

Examples of materials which can be pigmented with the pigment preparations of the present invention include: coatings, for example architectural coatings, industrial coatings, automotive coatings, radiation-curable coatings; paints, including paints for building exteriors and building interiors, for example wood paints, lime washes, distempers, emulsion paints; solventborne printing inks, for example offset printing inks, flexographic printing inks, toluene gravure printing inks, textile printing inks, radiation-curable printing inks; waterborne inks, including inkjet inks; color filters; building materials (water is typically added only after building material and granular pigment have been dry mixed), for example silicate render systems, cement, concrete, mortar, gypsum; bitumen, caulks; cellulosic materials, for example paper, paperboard, cardboard, wood and woodbase, which can each be coated or otherwise finished; adhesives; film-forming polymeric protective colloids as used for example in the pharmaceutical industry; cosmetic articles; detergents.

The pigment preparations of the present invention are very useful for coloring plastics of all kinds. The following classes and types of plastics may be mentioned by way of example:
modified natural materials:
thermosets, eg casein plastics; thermoplastics, eg cellulose nitrate, cellulose acetate, cellulose mixed esters and cellulose ethers;
synthetic plastics:
polycondensates: thermosets, eg phenolic resin, urea resin, thiourea resin, melamine resin, unsaturated polyester resin, allylic resin, silicone, polyimide and polybenzimidazole; thermoplastics, eg polyamide, polycarbonate, polyester, polyphenylene oxide, polysulfone and polyvinyl acetal;
addition polymers: thermoplastics, eg polyolefins, such as polyethylene, polypropylene, poly-1-butene and poly-4-methyl-1-pentene, ionomers, polyvinyl chloride, polyvinylidene chloride, polymethyl methacrylate, polyacrylonitrile, polystyrene, polyacetal, fluoropolymers, polyvinyl alcohol, polyvinyl acetate and poly-p-xylylene and also copolymers, such as ethylene-vinyl acetate copolymers, styrene-acrylonitrile copolymers, acrylonitrile-butadiene-styrene copolymers, polyethylene glycol terephthalate and polybutylene glycol terephthalate;
polyadducts: thermosets, eg epoxy resin and crosslinked polyurethanes; thermoplastics, eg linear polyurethanes and chlorinated polyethers.

Advantageously, plastics are colorable with the pigment preparations of the present invention by minimal energy input, for example by conjoint extrusion (preferably using a single- or twin-screw extruder), rolling, kneading or grinding. The plastics can be present at that stage as plastically deformable masses or melts and be processed into moldings, film and fiber.

The pigment preparations of the present invention are also notable in plastics coloration for altogether advantageous application properties, especially for good color properties, in particular high color strength and brilliance, and the good rheological properties of the plastics which have been colored with them, especially for low pressure-filter values (high filter lifetimes) and good spinnability.

EXAMPLES

Production and Testing of Inventive Pigment Preparations

The pigment preparations were produced by ball milling a suspension of x g of finished pigment (A), y g of additive (B) and if appropriate z g of additive (C) in 150 g of water (in the case of pH values <7, adjusted to pH 7 by addition of 25% by weight aqueous sodium hydroxide solution) to a $d_{50}$ value of <1 µm and then spray drying the millbase in a laboratory spray tower (Mini Spray Dryer B-191, from Büchi; gas inlet temperature 170° C., gas outlet temperature 70° C.).

The color strength of the pigment preparations was determined colorimetrically in white reduction (reported in terms of the DIN 55986 coloring equivalences CE) in a waterborne emulsion paint. To this end, a mixture of in each case 1.25 g of pigment preparation and 50 g of a waterborne styrene/acrylate-based test binder having a white pigment content of 16.4% by weight ($TiO_2$, Kronos 2043) (BASF test binder 00-1067) was homogenized in a 150 ml plastic cup by running a high speed stirrer at 1500 rpm for 3 min. The color obtained was then drawn down on a black and white test card using a 100 µm wire-wound film applicator and dried for 30 min.

The respective analogous emulsion paints prepared using commercially available aqueous formulations of the pigments were assigned the CE value 100 (standard). CE values <100 denote a higher color strength than standard, CE values >100 accordingly denote a lower color strength.

The table hereinbelow lists the compositions of the pigment preparations produced. The levels of the additives (B) and (C) are based on the dissolved polymer itself when the polymers were used in solution. The additives (B) and (C) used were as follows:
(B): aqueous solution of an anionic polyurethane oligomer (solids content: 25%; $M_w$: 8000, Borchi® GEN SN 95)
(C1): block copolymer based on ethylenediamine/propylene oxide/ethylene oxide having an ethylene oxide content of 40% by weight and an average molecular weight $M_n$ of 12 000
(C2): aqueous solution of a copolymer consisting of 50 mol % isobutene, 47 mol % maleic acid and 3 mol % $C_{18}$ olefin (solids content: 25% by weight; pH: 8; $M_w$: 10 000).

TABLE

| Ex. | Pigment (A) | x g | y g additive (B) | $z_1$ g additive (C1) | $z_2$ g additive (C2) | CE |
|---|---|---|---|---|---|---|
| 1 | P. Yellow 184 | 80 | 20 | — | 10 | 90 |
| 2 | P. Yellow 74 | 75 | 10 | 15 | — | 85 |
| 3 | P. Yellow 74 | 75 | 10 | — | 15 | 88 |
| 4 | P. Black 7 | 80 | 15 | 5 | — | 90 |
| 5 | P. Red 112 | 80 | 10 | 10 | — | 95 |
| 6 | P. Blue 15:3 | 80 | 10 | 10 | — | 95 |
| 7 | P. Violet 23 | 80 | 10 | 10 | — | 87 |

We claim:
1. A solid pigment preparation consisting essentially of
(A) from 60% to 95% by weight of at least one pigment,
(B) from 2.5% to 35% by weight of at least one water-soluble surface-active additive based on a polyurethane having an average molecular weight of from 500 to 250,000 and which is based on a reaction product of polyfunctional isocyanate (Ba) with an organic compound (Bb) comprising at least two isocyanate-reactive hydroxyl groups per molecule, wherein the organic compound (Bb) is selected from the group consisting of a polyetherdiol, a polyesterdiol, a lactone-based polyesterdiol, a diol having up to 12 carbon atoms, a triol having up to 12 carbon atoms, a dihydroxy carboxylic acid, a dihydroxy sulfonic acid, a dihydroxy phosphonic acid, a polycarbonatediol, a polyhydroxyolefin and a polysiloxane having on average at least two hydroxyl groups per molecule; and
(C) from 2.5% to 35% by weight of at least one nonionic water-soluble surface-active additive (C1) based on polyether or of an anionic water-soluble surface-active additive other than additives (B) which is based on polymers of ethylenically unsaturated carboxylic acid (C2) which is a homopolymer of an ethylenically unsaturated dicarboxylic acid, or a copolymer of an ethylenically unsaturated dicarboxylic acid, optionally comprising an interpolymerized vinyl monomer with no acid function, wherein the non-ionic additive (C1) is a reaction product of an alkylene oxide with an amine.
2. The pigment preparation according to claim 1 in the form of granules having an average particle size in the range from 50 to 5000 µm and a BET surface area of ≤15 $m^2/g$.

3. A process for producing a pigment preparation according to claim 1, which comprises wet-comminuting the pigment (A) in an aqueous suspension which comprises some or all of the additive (B) and, optionally the additive (C) and then drying the suspension, after the rest of the additive (B) and (C) have been added.

4. A process for colouring macromolecular organic and/or inorganic materials, which comprises incorporating a pigment preparation according to claim 1 in the macromolecular organic and inorganic material by stirring or shaking.

5. The process according to claim 4, wherein the organic and/or inorganic materials are contained in composition which is a coating, a paint, an ink or a finish system, the composition comprising a liquid phase comprising water, an organic solvent or mixtures of water and an organic solvent.

6. A process for colouring a plastic, which comprises incorporating pigment preparations according to claim 1 in the plastic by extruding, rolling, kneading or milling.

7. A process for colouring macromolecular organic and/or inorganic materials, which comprises incorporating a pigment preparation according to claim 2 in the macromolecular organic and inorganic material by stirring or shaking.

8. A process for colouring a plastic, which comprises incorporating pigment preparations according to claim 2 in the plastic by extruding, rolling, kneading or milling.

9. The pigment preparation according to claim 1, having a CE value of less than 100.

\* \* \* \* \*